United States Patent
Reinikainen et al.

(10) Patent No.: US 10,442,998 B2
(45) Date of Patent: Oct. 15, 2019

(54) METHOD AND APPARATUS FOR PRODUCING A CHEMICAL COMPOUND AND THE PRODUCED CHEMICAL COMPOUND

(71) Applicant: TEKNOLOGIAN TUTKIMUSKESKUS VTT OY, Espoo (FI)

(72) Inventors: Matti Reinikainen, Vtt (FI); Janne Hulkko, Vtt (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 15/735,059

(22) PCT Filed: Jun. 9, 2016

(86) PCT No.: PCT/FI2016/050409
§ 371 (c)(1),
(2) Date: Dec. 8, 2017

(87) PCT Pub. No.: WO2016/198744
PCT Pub. Date: Dec. 15, 2016

(65) Prior Publication Data

US 2018/0179449 A1  Jun. 28, 2018
US 2019/0031962 A2  Jan. 31, 2019
US 2019/0169507 A2  Jun. 6, 2019

(30) Foreign Application Priority Data

Jun. 12, 2015  (FI) ..................................... 20155453

(51) Int. Cl.
*C10G 2/00*    (2006.01)
*C07D 307/60*  (2006.01)
(Continued)

(52) U.S. Cl.
CPC .............. *C10G 2/332* (2013.01); *B01J 23/78* (2013.01); *B01J 29/40* (2013.01); *C07C 1/044* (2013.01);
(Continued)

(58) Field of Classification Search
CPC  C10G 2/232; C10G 2/341; C10G 2300/1011; C10G 2400/02; B01J 35/0006;
(Continued)

(56) References Cited

U.S. PATENT DOCUMENTS 4,036,780 A   7/1977  Suzuki et al.
6,348,132 B1  2/2002  Zhang et al.
(Continued)

FOREIGN PATENT DOCUMENTS

WO    9611193     4/1996
WO    2014190161  11/2014
WO    2015052379  4/2015

OTHER PUBLICATIONS

International Search Report for PCT/FI2016/050409, Completed by the Finnish Patent and Registration Office dated Sep. 29, 2016, 4 Pages.
(Continued)

*Primary Examiner* — Jafar F Parsa
(74) *Attorney, Agent, or Firm* — Brooks Kushman P.C.

(57) ABSTRACT

A method and an apparatus for producing a chemical compound from biomass based raw material. The bio-mass based raw material is gasified in a gasification device for forming a gasification gas, the gasification gas is treated in the reactor which includes at least one catalyst layer including Fe-based catalyst for forming a hydrocarbon composition, at least one hydrocarbon fraction including olefins is recovered from the hydrocarbon composition, and a chemical compound is formed from the hydrocarbon fraction.
(Continued)

Further, the invention relates to the produced chemical compound.

9 Claims, 4 Drawing Sheets

(51) Int. Cl.
| | |
|---|---|
| *B01J 23/78* | (2006.01) |
| *B01J 29/40* | (2006.01) |
| *C07C 1/04* | (2006.01) |
| *C07C 2/76* | (2006.01) |
| *C07C 7/04* | (2006.01) |
| *C07C 5/41* | (2006.01) |
| *C07C 51/54* | (2006.01) |
| *C07C 51/567* | (2006.01) |
| *C10J 3/82* | (2006.01) |
| *C10J 1/207* | (2012.01) |
| *C10J 1/213* | (2012.01) |
| *B01J 23/745* | (2006.01) |
| *D21H 21/16* | (2006.01) |

(52) U.S. Cl.
CPC .............. *C07C 1/0485* (2013.01); *C07C 2/76* (2013.01); *C07C 5/41* (2013.01); *C07C 7/04* (2013.01); *C07C 51/54* (2013.01); *C07C 51/567* (2013.01); *C07D 307/60* (2013.01); *C10G 2/00* (2013.01); *C10J 1/207* (2013.01); *C10J 1/213* (2013.01); *C10J 3/82* (2013.01); *B01J 23/745* (2013.01); *C07C 2523/745* (2013.01); *C07C 2529/40* (2013.01); *C10G 2300/1011* (2013.01); *C10G 2400/20* (2013.01); *C10G 2400/22* (2013.01); *C10J 2300/092* (2013.01); *C10J 2300/0916* (2013.01); *C10J 2300/1659* (2013.01); *D21H 21/16* (2013.01); *Y02E 50/32* (2013.01); *Y02P 20/52* (2015.11)

(58) Field of Classification Search
CPC . B01J 23/745; B01J 23/75; C10L 1/06; C10L 2290/42; C10L 2270/023; C10L 2200/0492; C10L 2290/543; Y02P 30/20; C07C 57/00; C07C 57/13
See application file for complete search history.

(56) References Cited

U.S. PATENT DOCUMENTS

| | | |
|---|---|---|
| 2012/0015411 A1 | 1/2012 | Dubois |
| 2013/0143972 A1 | 6/2013 | Townsend et al. |
| 2016/0024393 A1 | 1/2016 | Beech, Jr. et al. |

OTHER PUBLICATIONS

Finnish Search Report for Finnish Application No. FI 20155453, Completed by the Finnish Patent and Refistration Office dated Jan. 12, 2016, 1 Page.
Centi G. et al., "Mechanistic Aspects of Maleic Anhydride Synthesis From C4 Hydrocarbons Over Phosphorus Vanadium Oxide,", Chemical Reviews, American Chemical Society, U.S. vol. 88, Jan. 1, 1988, pp. 55-80. (XP001118496).
Extended European Search Report for EP Application 16806948.2, dated Jan. 7, 2019.

METHOD AND APPARATUS FOR PRODUCING A CHEMICAL COMPOUND AND THE PRODUCED CHEMICAL COMPOUND

CROSS-REFERENCE TO RELATED APPLICATION

This application is the U.S. national phase of PCT Application No. PCT/FI2016/050409 filed on Jun. 9, 2016, which claims priority to FI Patent Application No. 20155453 filed on Jun. 12, 2015, the disclosures of which are incorporated in their entirety by reference herein.

FIELD OF THE INVENTION

The invention relates to a method for producing a chemical compound from biomass based raw material and an apparatus for producing a chemical compound from biomass based raw material. Further, the invention relates to a chemical compound obtained by the method.

BACKGROUND OF THE INVENTION

Known from the prior art is that different chemical components can be produced from fossil source materials. In the art of the chemical manufacturing there is a need for a bio based alternative.

It is known from the prior art that maleic anhydride is produced practically from fossil source materials. From US 2012/0015411 is known a process for manufacturing maleic anhydride from renewable materials by fermentation and by oxidation using vanadium or molybdenum based catalyst. Further, from US 2013/0143972 is known a process for producing chemicals, such as alcohols, carboxylic acids, esters, aldehydes, olefins and polymers, from biomass by forming a product gas at a pressure of at least 10 bar and by treating the product gas in an alcohol synthesis.

It is known from the prior art that alkenyl succinic anhydride is produced from fossil source materials.

Further, it is known from the prior art that carbonaceous raw materials can be gasified and processed in the Fischer-Tropsch (F-T) synthesis. In the basic form of the F-T synthesis, the gas from the carbonaceous raw material is converted to straight chain hydrocarbons in the presence of a cobalt catalyst at temperature of 200-250° C. and pressure of 20-40 bar. Typically, diesel and other middle-distillates are produced in the F-T synthesis.

Objective of the Invention

The objective of the invention is to disclose a new type method and apparatus for producing a chemical compound. Further, the objective of the invention is to produce a new chemical compound from the biomass based raw material.

SUMMARY

The method and apparatus and chemical compound according to the invention are characterized by what has been presented in the claims.

The invention is based on a method for producing a chemical compound from biomass based raw material. According to the invention, the biomass based raw material is gasified in a gasification device for forming a gasification gas, the gasification gas is treated in the reactor which comprises at least one catalyst layer including Fe-based catalyst for forming a hydrocarbon composition comprising olefins, at least one hydrocarbon fraction comprising olefins is recovered from the hydrocarbon composition, and a chemical compound is formed from the hydrocarbon fraction.

The apparatus of the invention comprises a gasification device in which the biomass based raw material is gasified to form a gasification gas, and a feeding device for feeding the biomass based raw material to a gasification device, and a reactor comprising at least one catalyst layer in which the gasification gas is treated by means of Fe-based catalyst for forming a hydrocarbon composition, and a recovery device for recovering at least one hydrocarbon fraction comprising olefins, and at least one treatment device for forming a chemical compound from the hydrocarbon fraction.

Further, the invention is based on a chemical compound which is obtainable by the method according to the invention.

In this context, the biomass based raw material refers to any biomass material or biomass based material or any combination of different biomass materials. The biomass material may contain also other materials than biomass but the biomass material contains at least 60% by weight biomass. Biomass may be forest residue, other woody biomass and/or agro biomass or the like.

In this context, the hydrocarbon composition contains olefins. In one embodiment, the hydrocarbon composition is rich in olefin hydrocarbons. Preferably, the hydrocarbon composition is a highly olefinic composition. Further, the hydrocarbon composition may contain also paraffines. Further, the hydrocarbon composition may contain other hydrocarbons.

As the gasification device can be used any suitable gasification device or gasifier. In one embodiment, the gasification device is a fluid bed gasifier. Preferably low pressure is used in the gasification device.

In one embodiment, the gasification gas is purified. In one embodiment, the gasification gas is filtered. In one embodiment, tars are removed, e.g. by reforming, from the gasification gas. In one embodiment, the gasification gas is cleaned so that sulphur level is below about 5 ppm before the reactor. Preferably, ultra-cleaning of the gas is not necessary. In one embodiment, the apparatus comprises a filtration device or a purifying device.

In one embodiment, the gasification gas is fed from the gasification device to the reactor. In one embodiment, the apparatus comprises a second feeding device for feeding the gasification gas to the reactor. In one embodiment, the gasification gas is treated by supplying the gasification gas through the catalyst layer of the reactor in order to form the hydrocarbon composition. Preferably, H2/CO ratio of the gasification gas needs not to be adjusted before the reaction.

Any suitable reactor known per se can be used in the catalytic reaction. Preferably, the reactor can be a fixed bed reactor, a slurry reactor, other suitable reactor or the like. Preferably, the reactor is a continuous reactor. In one embodiment, the reactor is Fischer-Tropsch type reactor (FT-reactor). In one embodiment, the reactor is a modified Fischer-Tropsch reactor.

In one embodiment, reaction pressure is between 1-10 bar, preferably 3-8 bar, more preferably 4-6 bar in the reactor. In one embodiment, the reaction pressure is adjusted according to the gasification pressure. Because pressure is typically below 5 bar in the gasification so same pressure area can be used in the catalytic reactions when the gasification gas from the gasification is processed in the reactor. Preferably low pressure is used in the reactor. When lower pressure is used in the reaction then sulphur absorbs more weakly to the catalyst. Further, lower pressure facilitates equipment engineering.

In one embodiment, the apparatus of the invention comprises a pressure controlling device to control the pressure in the catalyst layer. In one embodiment, the pressure controlling device is arranged in connection with the reactor.

In one embodiment, temperature of the catalyst layer is between 200-350° C. in the reactor. Preferably, high temperature is used in the reactor. Preferably, temperature may be controlled during the catalytic reaction. Preferably, temperature is selected so that sufficient reaction rate and desired product fraction can be achieved. In low pressure the activity is lower and then higher temperature is used. In the higher temperature lighter product can be produced.

In one embodiment, the apparatus of the invention comprises a temperature controlling device to control the temperature in the catalyst layer. In one embodiment, the temperature controlling device is arranged in connection with the reactor.

In the reactions of the catalyst layer the hydrocarbon composition is produced by means of the Fe-based catalyst. Fe-based catalyst means any Fe based catalyst or any modified Fe based catalyst. In one embodiment, an amount of olefinic hydrocarbons is over 60% by weight, preferably over 70 by weight, more preferably over 80% by weight, most preferably over 90% by weight, from hydrocarbons after the Fe-based catalyst layer. In one embodiment, sulphur may be removed from the synthesis gas in connection with the catalyst layer. Preferably, iron based catalyst acts both as the catalyst layer and as a sulphur removing bed. In one embodiment, sulphur may be removed in an additional step, preferably before the catalyst layer. In one embodiment, at least one promoter is added to modify the catalyst.

In this context, the catalyst layer means any catalyst layer, catalyst bed or the like.

By means of the invention the hydrocarbon composition can be formed by the gasification and by reaction with low pressure and Fe-catalyst.

In one embodiment, water may be removed from the hydrocarbon composition.

In one embodiment, the hydrocarbon composition is fractionated for recovering at least one hydrocarbon fraction comprising olefins. In one embodiment, the fractionating is performed after the forming of the hydrocarbon composition in the reactor which comprises at least one catalyst layer including Fe-based catalyst. In one embodiment, the fractionating is performed after a treatment of the hydrocarbon composition, e.g. after the aromatization. In one embodiment, the apparatus comprises a fractionating device for recovering at least one hydrocarbon fraction comprising olefins.

In one embodiment, the hydrocarbon composition is condensated by water before or in connection with the fractionating. In one embodiment, the apparatus comprises a condensation device.

In one embodiment, hydrogen is separated from the hydrocarbon composition after the forming of the hydrocarbon composition in the reactor which comprises at least one catalyst layer including Fe-based catalyst. In one embodiment, light hydrocarbons, e.g. C1 and C2 hydrocarbons, are separated from the hydrocarbon composition after the forming of the hydrocarbon composition. In one embodiment, non-condensable hydrocarbons are removed. In one embodiment, condensable hydrocarbons are introduced to the aromatization or to other treatment.

In one embodiment, the fractionating is performed by using distillation. In one embodiment, the apparatus comprises a distillation device. In one embodiment, the fractionating is performed by using separation. In one embodiment, the apparatus comprises a separation device for fractionating the hydrocarbon composition. In one embodiment, the fractionating is performed by using crystallisation. Alternatively, the fractionating may be performed by using any suitable fractionating device known per se.

Preferably, at least one hydrocarbon fraction is recovered in connection with the fractionating. In one embodiment, one hydrocarbon fraction is recovered. In one embodiment, at least two hydrocarbon fractions are recovered. In one embodiment, all the desired fractions are recovered by means of the same device. Alternatively, the desired fractions may be recovered by means of different devices.

Preferably, the hydrocarbon fraction comprises olefins and paraffines. In one embodiment, the hydrocarbon fraction comprising C3 and C4+ olefins and paraffines is separated from the hydrocarbon composition. In one embodiment, the hydrocarbon fraction comprising C4 olefins and paraffines is separated from the hydrocarbon composition. In one embodiment, the hydrocarbon fraction comprising C6-C18 α-olefins, in one embodiment C8-C16 α-olefins, is separated from the hydrocarbon composition. Each hydrocarbon fraction may contain also other agents, compounds, hydrocarbons, distillates or components. Preferably, the hydrocarbon fraction is in the liquid form.

In one embodiment, the hydrocarbon fraction includes 50-100% by weight, preferably 60-100% by weight and more preferable 70-100% by weight, $C_3$ and $C_{4+}$ hydrocarbons. In one embodiment, the hydrocarbon fraction includes 50-100% by weight, preferably 60 100% by weight and more preferable 70-100% by weight, $C_4$ hydrocarbons. In one embodiment, the hydrocarbon fraction includes 50-100% by weight, preferably 60-100% by weight and more preferable 70-100% by weight, $C_6$-$C_{18}$ hydrocarbons.

In one embodiment, the hydrocarbon fraction is treated in order to form the chemical compound selected from the group consisting of maleic anhydride, alkenyl succinic anhydride and their combinations.

In one embodiment, the hydrocarbon composition is treated by an aromatization which is performed at normal pressure and in the presence of a zeolite catalyst for forming the hydrocarbon composition comprising aromatics. In one embodiment, the desired hydrocarbon fraction is recovered by fractionating after the aromatization. The fractionating can be performed such as presented above.

In one embodiment, the hydrocarbon fraction, preferably including C3 and C4+ olefins and paraffines, is treated by an aromatization which is performed at normal pressure and in the presence of a zeolite catalyst for forming aromatics. In one embodiment, hydrogen is removed from the aromatization reactor, e.g. using a membrane. In one embodiment, at least benzene fraction is separated from the aromatics. In one embodiment, the aromatics are fractionated, e.g. by distillation and/or crystallisation. In one embodiment, the benzene fraction contains benzene and o-xylene. In one embodiment, C4 fraction is separated from the aromatics. In one embodiment, the benzene fraction is partially oxidized for forming maleic anhydride.

In one embodiment, the hydrocarbon fraction is treated by an aromatization which is performed at normal pressure and in the presence of a zeolite catalyst for forming aromatics, the aromatics are fractionated and at least benzene fraction is separated from the aromatics, and the benzene fraction is partially oxidized for forming maleic anhydride.

In this context, the zeolite catalyst means any zeolite based catalyst or any modified zeolite based catalyst. In one embodiment, the zeolite catalyst is ZSM-5 zeolite catalyst.

In one embodiment, temperature is between 320-550° C. during the aromatization.

Preferably, water is not need to remove from the hydrocarbon composition or hydrocarbon fraction before the aromatization. Water protects the catalyst during the aromatization. Similarly, this procedure can act as a purification of waste water.

In one embodiment, water is removed from a product of the aromatization.

In one embodiment, the hydrocarbon fraction, consisting of C4 olefins and paraffines, is partially oxidized for forming maleic anhydride, preferably after the fractionating of the hydrocarbon composition. In one embodiment, the hydrocarbon fraction, consisting of C4 olefins and paraffines, is partially oxidized for forming maleic anhydride after the aromatization and fractionating. Preferably, said hydrocarbon fraction does not include substantially other olefins or paraffines than C4 olefins and paraffines.

In one embodiment, the hydrocarbon fraction, preferably including α-olefins, such as C6-C18α-olefins, more preferably C8-C16 α-olefins, is treated by a reaction with maleic anhydride so that olefins react with maleic anhydride for forming alkenyl succinic anhydride, in one embodiment octenyl succinic anhydride. The reaction can be carried out in any suitable reactor, e.g. a mixing reactor. In one embodiment, the reaction is carried out at temperatures between 150-250° C. Maleic anhydride may be biobased maleic anhydride, e.g. from a process defined in this context or from other manufacturing process of maleic anhydride.

Other hydrocarbon fractions, which are not recovered, can be utilized in a manufacturing of bio-aromatics or other chemicals or as fuel or energy.

In one embodiment, the chemical compound is used and utilized as a final product, as a component for producing a final product or as an energy component as such or after the additional treatment. In one embodiment, the final product is a chemical, e.g. polyester, coupling agent, e.g. maleic anhydride based coupling agent, biobased paper additive, e.g. paper sizing agent, energy component or the like. In one embodiment, a final product comprises maleic anhydride, alkenyl succinic anhydride and their combinations.

In one embodiment, the method and apparatus of the present invention is used and utilized in the manufacturing of the chemicals, in the manufacturing of the maleic anhydride, in the manufacturing of the alkenyl succinic anhydride, in the manufacturing of the paper sizing agent, in the energy production or in their combinations.

By means of the invention the desired chemical product can be formed simply from biomass based raw material. Thanks to the invention the chemical compounds with good quality can be manufactured successfully. Thanks to the invention reactions for forming chemical compounds can be carried out at a low pressure. By means of the invention biomass can be utilized very efficiently to valuable products.

According to the invention, biomass gasification followed by modified Fischer-Tropsch reaction at very moderate reaction conditions enables cost efficient production of maleic anhydride from a wide range of biomass. The utilization of each reaction product ensures the optimal biomass utilization and value-addition. For instance, C4-gases would usually be used as LPG whereas now they are converted to biochemical. Further, according to the invention fully biobased high-value paper chemical can be manufactured.

The method and apparatus of the invention offers a possibility to produce the chemical compounds cost-effectively and energy-effectively. The present invention provides an industrially applicable, simple and affordable way of producing chemical compounds from biomass. The method and apparatus of the present invention is easy and simple to realize as a production process, also as a small scale process.

LIST OF FIGURES

In the following section, the invention will be described with the aid of detailed exemplary embodiments, referring to the accompanying figure wherein.

DETAILED DESCRIPTION OF THE INVENTION

Example 1

Figure 1:
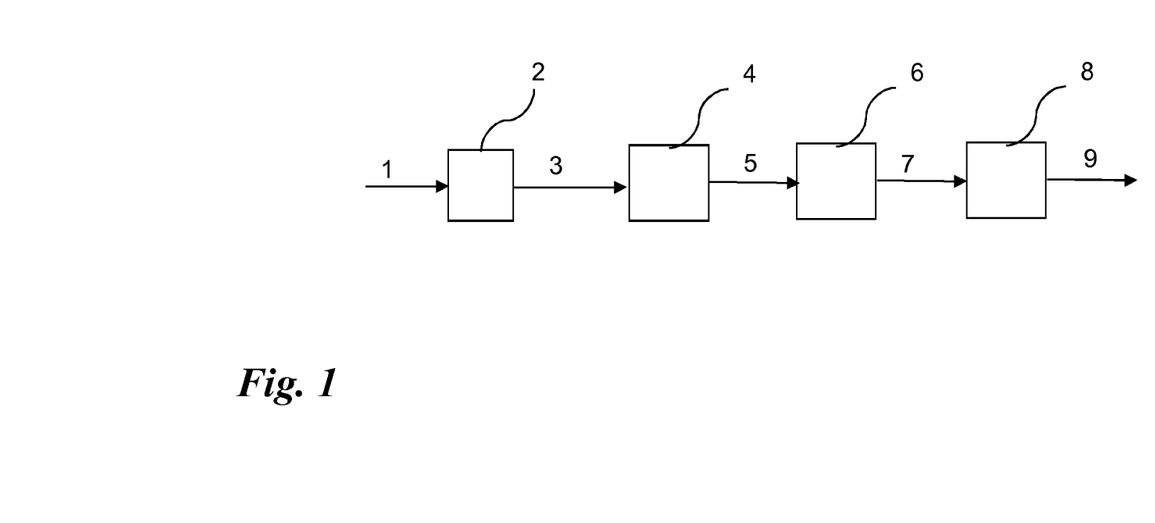
FIG. 1 presents one embodiment according to the invention.

FIG. 1 presents the method according to the invention for producing a chemical compound.

The chemical compound (9) is formed from biomass based raw material (1). The biomass based raw material (1) is gasified in a gasification device (2) in order to form a gasification gas (3). Preferably, the gasification gas is cleaned.

The gasification gas (3) is fed into a reactor (4) which comprises the catalyst layer containing Fe-based catalyst, and the gasification gas is treated in the reactor, under pressure between 1-10 bar, in order to form a hydrocarbon composition (5). From the reactor (4) the hydrocarbon composition (5) is fed into a fractionating device (6), such as a distillation device, in which the hydrocarbon composition (5) is fractionated and at least one hydrocarbon fraction (7) is recovered from the hydrocarbon composition. The hydrocarbon composition may be condensated by water before the fractionating. The hydrocarbon fraction (7) is treated in the treatment step (8), and the chemical compound is formed.

The reactor (4) comprises a temperature controlling device and a pressure controlling device which are arranged to control the temperature and pressure in the catalyst layer of the reactor. Preferably, sulphur is mainly removed from the gasification gas in the reactor (4) in which the catalyst layer acts as a sulphur removing layer.

Example 2

Figure 2:
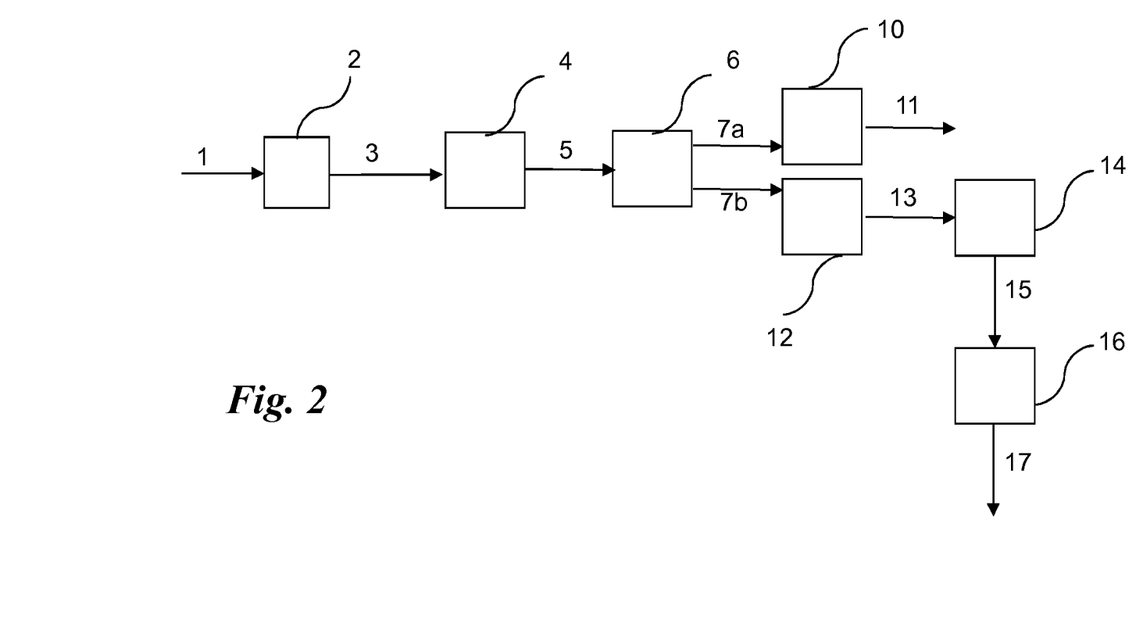
FIG. 2 presents another embodiment according to the invention.

FIG. 2 presents the method according to the invention for producing a maleic anhydride.

The maleic anhydride (11,17) is formed from biomass based raw material (1). The biomass based raw material (1) is gasified in a gasification device (2) in order to form a gasification gas (3). Preferably, the gasification gas is cleaned.

The gasification gas (3) is fed into a modified Fischer-Tropsch reactor (4) which comprises the catalyst layer containing Fe-based catalyst, and the gasification gas is treated in the reactor, under pressure between 1-10 bar, in order to form a hydrocarbon composition (5). The hydrocarbon composition (5) comprises olefins and also paraffines. From the reactor (4) the hydrocarbon composition (5) is fed into a fractionating device (6), such as a distillation device, in which the hydrocarbon composition (5) is fractionated and at least two hydrocarbon fractions (7a and 7b) are recovered from the hydrocarbon composition. The first hydrocarbon fraction (7a) contains butenes and butanes. The second hydrocarbon fraction (7b) contains C3 and C4+ hydrocarbons, such as C3 and C4+ olefins and paraffines.

The first hydrocarbon fraction (7a) is partially oxidized (10) to the maleic anhydride (11).

The second hydrocarbon fraction (7b) is converted to aromatic hydrocarbons (13) in an aromatization reactor (12) under normal pressure and in the presence of a zeolite catalyst. The aromatic hydrocarbons (13) are fractionated (14), e.g. by distillation or crystallisation, and a benzene fraction (15) comprising benzene and o-xylene is separated from the aromatic hydrocarbons. The benzene fraction (15) is partially oxidized (16) for forming the maleic anhydride (17).

The modified Fischer-Tropsch reactor (4) comprises a temperature controlling device and a pressure controlling device which are arranged to control the temperature and pressure in the catalyst layer of the reactor. Preferably, sulphur is mainly removed from the gasification gas in the reactor (4) in which the catalyst layer acts as a sulphur removing layer.

Example 3

Figure 3:
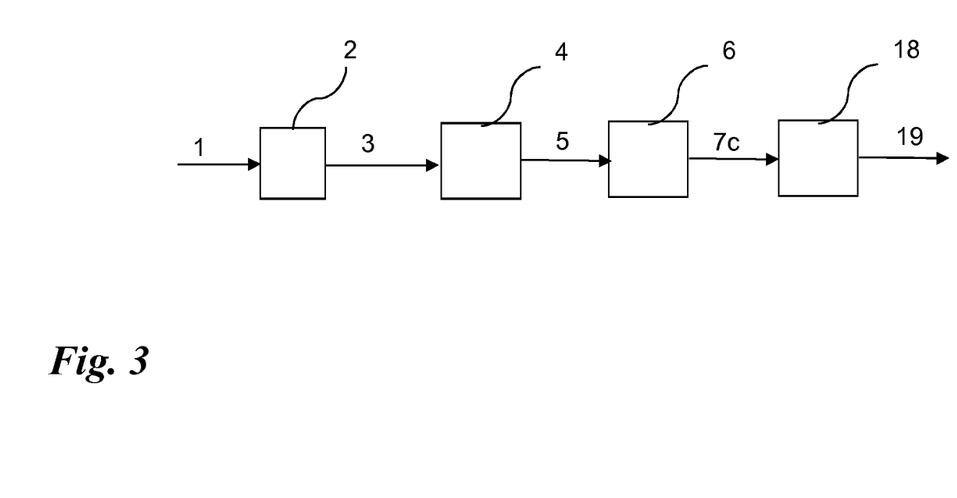
FIG. 3 presents another embodiment according to the invention.

FIG. 3 presents the method according to the invention for producing an alkenyl succinic anhydride (ASA).

The alkenyl succinic anhydride (19) is formed from biomass based raw material (1). The biomass based raw material (1) is gasified in a fluid bed gasifier (2) in order to form a gasification gas (3). Preferably, the gasification gas is cleaned.

The gasification gas (3) is fed into a modified Fischer-Tropsch reactor (4) which comprises the catalyst layer containing Fe-based catalyst, and the gasification gas is treated in the reactor, under pressure between 1-10 bar, in order to form a hydrocarbon composition (5). From the reactor (4) the hydrocarbon composition (5) is fed into a fractionating device (6), such as a distillation device, in which the hydrocarbon composition (5) is fractionated and at least one hydrocarbon fraction (7c) is recovered from the hydrocarbon composition. The hydrocarbon fraction (7c) contains C8-C16 α-olefins. The hydrocarbon fraction (7c) is treated by a reaction with maleic anhydride in a treatment device (18) so that olefins react with maleic anhydride for forming alkenyl succinic anhydride (19). The maleic anhydride may be biobased maleic anhydride, e.g. from a process according to example 2, or other maleic anhydride.

The reactor (4) comprises a temperature controlling device and a pressure controlling device which are arranged to control the temperature and pressure in the catalyst layer of the reactor. Preferably, sulphur is mainly removed from the gasification gas in the reactor (4) in which the catalyst layer acts as a sulphur removing layer.

Example 4

Forest residue wood chips were gasified in a circulating fluid bed gasifier equipped with a ceramic filter and a catalytic reformer. A slip stream of the gas was dried and purified using an adsorption bed. The purified gas was treated in a tubular reactor (stainless steel, inner diameter 12 mm) over a precipitated iron catalyst promoted by potassium. The reaction conditions were: GHSV 2000 h$^{-1}$, H$_2$/CO-ratio 1.4 (mol/mol), temperature 240° C. and pressure 5 bar. Under these conditions CO conversion was about 65% after 50 hours on stream. Water was separated from the reaction product and the hydrocarbon composition was analysed by gas chromatography. The composition and the share of olefins are shown in table 1.

TABLE 1

| Hydrocarbon product | mass-% | share of olefins/mass-% |
|---|---|---|
| C1 | 12.9 | — |
| C2 | 14.3 | 48.2 |
| C3 | 15.2 | 76.5 |
| C4 | 11.3 | 87.2 |
| C5 | 9.0 | 86.9 |
| C6 | 8.9 | 73.6 |
| C7 | 7.3 | 76.1 |
| C8 | 4.8 | 82.0 |
| C9 | 3.6 | 80.8 |
| C10 | 3.1 | 81.7 |
| C11 | 2.5 | 83.4 |
| C12 | 1.8 | 80.4 |
| C13 | 1.6 | 74.3 |
| C14 | 1.0 | 72.1 |
| heavier than C14 hydrocarbons | 2.7 | 71.1 |

Example 5

A highly olefinic hydrocarbon fraction was recovered from the product of Example 4 using distillation. The composition of the obtained fraction is shown in table 2. In addition to olefins the fraction contains also paraffines.

TABLE 2

| Hydrocarbon | mass-% |
|---|---|
| C9 | 0.2 |
| C10 | 5.0 |
| C11 | 18.4 |
| C12 | 23.9 |
| C13 | 20.1 |
| C14 | 13.6 |
| C15 | 8.3 |
| C16 | 5.8 |
| C17 | 2.9 |
| C18 | 1.7 |
| heavier than C18 | 0.2 |

A 300 ml laboratory autoclave was charged with a portion of the recovered fraction and maleic anhydride in a molar ratio of about 1.2:1. The autoclave was closed, filled with nitrogen and heated to 220° C. The reactor was kept at this temperature for 5 h. The reactor was mixed with a turbine mixer at 600 rpm. The obtained product contained ASA in a yield of 48%.

Example 6

Figure 4:
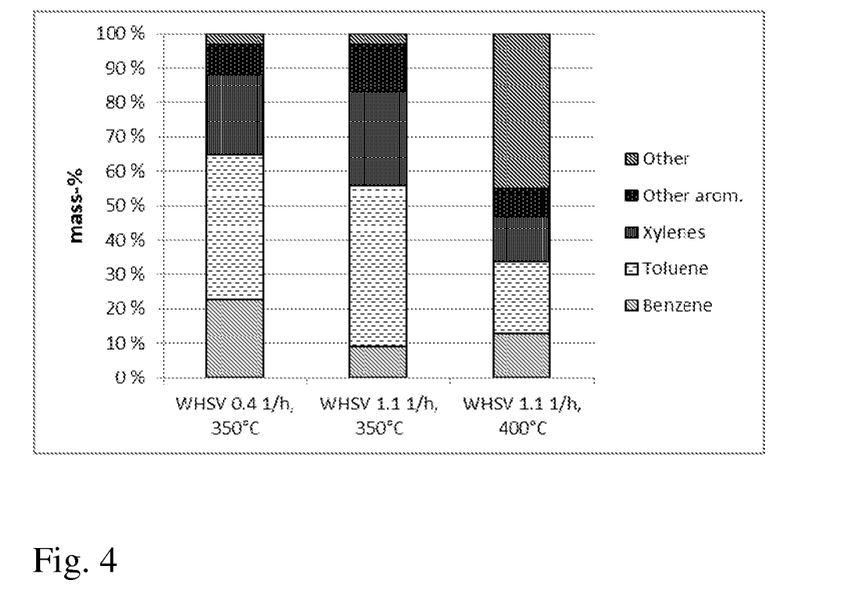
FIG. 4 presents test results.

Fischer-Tropsch type reaction (FT-reaction) was carried out using the same setup and reaction conditions as in example 4. The outlet of the back pressure valve controlling the reaction pressure of the FT-reaction was connected directly to an aromatization reactor which was a tubular reactor, made of stainless steel, with an inner diameter 40 mm. The aromatization reaction was carried out in the presence of a ZSM-5 zeolite catalyst promoted with Zn and La. The catalyst mass was selected to give a weight hourly space velocity (WHSV) of 0.4 or 1.1 g/($g_{cat}$ h). The reactor was heated with a furnace to temperatures of 350-400° C. and the reaction was carried out at atmospheric pressure. Water was separated from the product and the product was analysed using gas chromatography after the aromatization. The composition of the product is given in FIG. 4.

The parts and devices used in this invention are known per se in the art, and therefore they are not described in any more detail in this context.

The method and apparatus according to the invention is suitable in different embodiments for forming different kinds of chemical compounds.

The invention is not limited merely to the examples referred to above; instead many variations are possible within the scope of the inventive idea defined by the claims.

The invention claimed is:

1. A method for producing a chemical compound from biomass based raw material, the method comprising:
   gasifying the biomass based raw material in a gasification device forming a gasification gas,
   treating the gasification gas in a reactor which has a catalyst layer consisting essentially of a Fe-based catalyst for forming a hydrocarbon composition,
   recovering at least one hydrocarbon fraction comprising olefins from the hydrocarbon composition so that the hydrocarbon fraction comprising:
   C3 and C4+ olefins and paraffines,
   C4 olefins and paraffines, and/or
   C6-C18 α-olefins,
   are separated from the hydrocarbon composition, and
   treating the separated hydrocarbon fraction forming a chemical compound, with a material selected from the group consisting of: aromatics, maleic anhydride and/or alkenyl succinic anhydride, and the treatment is carried out such that the hydrocarbon composition or the hydrocarbon fraction comprising C3 and C4+ olefins and paraffines is treated by an aromatization which is performed at normal pressure and in the presence of a zeolite catalyst for forming aromatics, and/or the hydrocarbon fraction comprising C4 olefins and paraffines is partially oxidized forming maleic anhydride.

2. The method according to claim 1, wherein the reaction pressure in the gasification device is between 1-10 bar.

3. The method according to claim 1, wherein the temperature of the catalyst layer is between 200-350° C. in the reactor.

4. The method according to claim 1, wherein the hydrocarbon composition is condensated by water.

5. The method according to claim 1, wherein the hydrocarbon composition is fractionated for recovering at least one hydrocarbon fraction comprising olefins.

6. The method according to claim 5, wherein the fractionating of the hydrocarbon composition is performed by using distillation.

7. The method according to claim 1, further comprising:
   treating the C3 and C4+ olefins and paraffines by an aromatization performed at normal pressure and in the presence of a zeolite catalyst for forming aromatics,
   separating a benzene fraction from the aromatics, and
   partially oxidizing the benzene fraction forming maleic anhydride.

8. The method according to claim 1, wherein the hydrocarbon fraction comprising C6-C18 α-olefins is treated by a reaction with maleic anhydride so that olefins react with maleic anhydride for forming alkenyl succinic anhydride.

9. The method according to claim 1, further comprising removing sulphur from the at least one hydrocarbon fraction in a sulphur removing bed using a second Fe-based catalyst or a modified Fe-based catalyst.

* * * * *